(12) United States Patent
Lamb et al.

(10) Patent No.: US 7,608,831 B2
(45) Date of Patent: Oct. 27, 2009

(54) RADIOACTIVITY DOSE CALIBRATOR

(76) Inventors: James F Lamb, 8713 Dunaire Cir., Knoxville, TN (US) 37923; Lewis Carroll, 950 Gillman St., Berkeley, CA (US) 94710

( * ) Notice: Subject to any disclaimer, the term of this patent is extended or adjusted under 35 U.S.C. 154(b) by 0 days.

(21) Appl. No.: 12/405,926

(22) Filed: Mar. 17, 2009

(65) Prior Publication Data
US 2009/0236536 A1 Sep. 24, 2009

Related U.S. Application Data

(60) Provisional application No. 61/037,492, filed on Mar. 18, 2008.

(51) Int. Cl.
*G01T 1/02* (2006.01)
(52) U.S. Cl. .............................. 250/370.07; 250/507.1; 250/328; 600/5
(58) Field of Classification Search ............ 250/370.07, 250/507.1, 328; 600/5
See application file for complete search history.

(56) References Cited

U.S. PATENT DOCUMENTS

| | | | | |
|---|---|---|---|---|
| 4,401,108 A | * | 8/1983 | Galkin et al. | 600/5 |
| 5,274,239 A | * | 12/1993 | Lane et al. | 250/370.01 |
| 6,267,717 B1 | * | 7/2001 | Stoll et al. | 600/4 |
| 6,586,758 B2 | | 7/2003 | Martin | |
| 7,307,265 B2 | * | 12/2007 | Polsinelli et al. | 250/507.1 |
| 7,414,254 B2 | | 8/2008 | Polsinelli et al. | |
| 2005/0107698 A1 | * | 5/2005 | Powers et al. | 600/436 |

* cited by examiner

*Primary Examiner*—David P Porta
*Assistant Examiner*—Jessica L Eley
(74) *Attorney, Agent, or Firm*—Wildman, Harrold, Allen & Dixon LLP

(57) ABSTRACT

A radioactivity dose calibrator system measures the quantity of radioactive material contained in a sample-vial or syringe without removing the vial or syringe from its primary radiation shield. The system comprises a first radiation detector, a second radiation detector, a transportable, shielded radioactive material sample-holder, a signal-processing circuit and a video display.

12 Claims, 3 Drawing Sheets

RADIOACTIVITY DOSE CALIBRATOR

CROSS-REFERENCE TO RELATED APPLICATIONS

This application claims the benefit of provisional application Ser. No. 61/037,492 filed Mar. 18, 2008 by the above-named inventors.

FIELD OF THE INVENTION

This invention relates to instrumentation used for measuring a quantity of radioactive material dispensed in nuclear pharmacies.

BACKGROUND OF THE INVENTION

In the practice of nuclear medicine, certain radioactive isotopes are formulated in a nuclear pharmacy, or in a nuclear medicine "hot lab", where they are subdivided into units from a bulk source or combined with other materials to produce diagnostic and/or therapeutic agents referred to as radio-pharmaceuticals. These radio-pharmaceuticals are important products in health-care and in commerce, whose value—in terms of their diagnostic or pharmacologic effect as well as price—is generally proportional to the amount of radioactive material present in a given sample.

A unit-quantity of a radio-pharmaceutical is typically referred to as a dose. An essential step in the preparation of each dose is an accurate measurement—or calibration—of the amount of radioactivity which is present. The amount of radioactivity contained in the dose must be known to within a prescribed degree of precision; if the dose is too small, it will not produce the required diagnostic or therapeutic efficacy, and if the dose is too large, there may be undesired or dangerous side effects due to excess exposure to radiation. Whether the dose is prepared in the nuclear medicine lab or by a commercial nuclear pharmacy, its calibrated activity must also be verified by the physician before patient administration.

A typical dose calibrator 9 of the prior art is shown schematically in FIG. 1. This particular apparatus, familiar to those schooled in the art, is called an Ionization Chamber. The ionization chamber is typically configured as two thin-walled, cylindrical metallic shells 1, 2 arranged coaxially (shown in cut-away), and separated by an air-space 3. The two shells are electrically insulated from each other and from external contact. A high-voltage power supply 6 in series with a sensitive current-measuring meter or circuit 7 are connected to the inner and outer shells. A small vial or syringe 4 containing a dose to be measured is placed near the center of the chamber. The vial or syringe is an intense source of radiation emitting penetrating, high-energy photons at a rate which is proportional to the amount of activity present—expressed in Becqerels. One Becqerel equals 1 radioactive decay per second. An older, but still widely used, unit of radioactivity is the Curie which is defined as $3.7 \times 10^{10}$ radioactive decays per second.

The energetic photons interact with the air in the annular space 3, and also in the chamber walls 1, 2 liberating secondary electrons which also interact with air in the annular space. These interactions ionize the air, generating a small electrical current, which is measured by the current-measuring meter or circuit 7. This current is generally proportional to the amount of radioactivity present in the sample vial or syringe.

As a practical matter, the overall dimensions of the ion chamber are generally rather large compared with the dimensions of the vial or syringe in order to insure uniformity of response, i.e., independent of small deviations from ideal symmetry of placement of the sample, and to provide sufficient ion current, which is generally proportional to the intensity of radiation, but also proportional to the volume of ionized air within the annular space of the chamber. The current to be measured may typically range from a few pico amperes for a small dose of radio-pharmaceutical, up to several tens of nano-amperes for a 'bulk' shipment.

A crucial attribute of a properly configured dose calibrator is that (for a given isotope) the measured current signal should be proportional only to the amount of activity present, i.e., depending only on the number of radioactive decays per second, and should not vary substantially because of small variations in sample volume or small changes in placement of the sample within the chamber.

Finally, the ion-chamber dose calibrator must be shielded so as to prevent false readings due to ambient background radiation that may be present in the lab and—more important—to protect the pharmacist or technician from exposure to penetrating radiation from the dose being measured. The shield 8 is typically configured as a cylinder surrounding the chamber (shown in cut away view.) The mass of shielding depends on the size of the chamber and on the particular radioactive materials being processed, and may require as much as a four inch thickness of lead, or equivalent dense material when operated in a busy, commercial-scale radio-pharmacy formulating doses for Positron Emission Tomography (PET). Doses must also be removed from their primary shield in which they are shipped and/or stored before making an ion chamber measurement, exposing personnel to unshielded radiation.

OBJECTS AND SUMMARY OF THE INVENTION

The object of the present invention is to provide a novel implementation of a radioactivity dose calibrator for use in nuclear pharmacies which:

- is compact and relatively easy to shield, as compared to a "traditional" ion chamber of the prior art;
- provides a more rapid and more precise reading due to higher intrinsic detection efficiency, as compared to a "traditional" ion chamber of the prior art;
- provides an output signal which is proportional to the amount of radioactivity present—within a pre-determined degree of precision—but is substantially invariant to physical placement, provided the radioactive source material is located within a prescribed volume envelope;
- provides a rapid and simple verification of placement of the sample within the prescribed volume envelope; and
- is capable of measuring an output dose of a radioactive material without removing the dose from its primary shield.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

Figure 1:
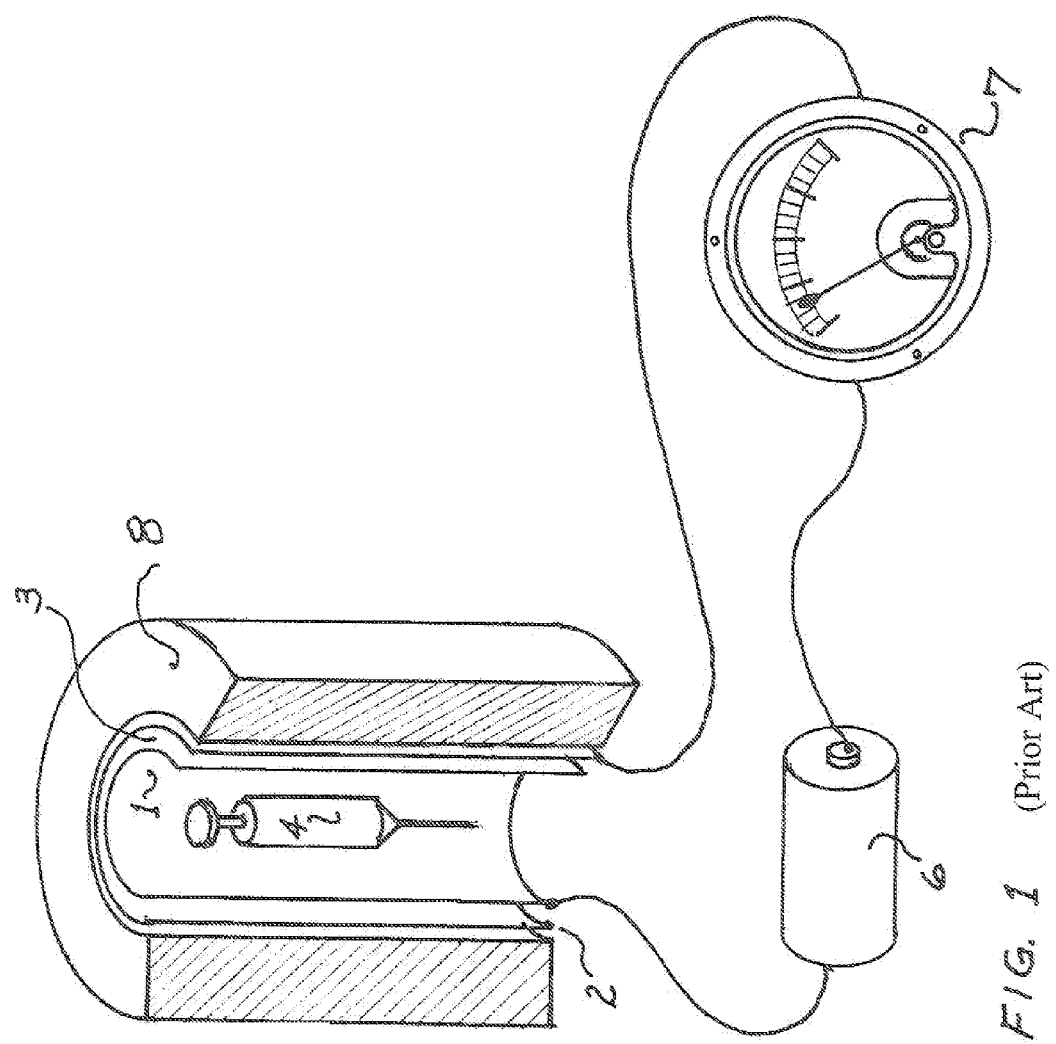
FIG. 1 is a schematic illustration of a prior art radiation dose calibrator.

Table I lists the reference numerals associated with the various elements and components listed in the figures and discussed in this application.

TABLE I

| | |
|---|---|
| 1. | Ion chamber inner shell |
| 2. | Ion chamber outer shell |
| 3. | Annular air space |
| 4. | Sample vial or syringe containing radioactive material |
| 5. | |
| 6. | High voltage power supply |
| 7. | Sensitive current meter or its functional equivalent |
| 8. | Shielding around ion chamber |
| 9. | Prior Art |
| 10. | First radiation detector |
| 11. | First detector shield |
| 12. | Second radiation detector |
| 13. | Second detector shield |
| 14. | Sample vial or syringe containing radioactive material |
| 15. | Main portion of transportable radiation shield, with end caps removed |
| 15A | First removable end cap - removed as used in this invention |
| 15B | Second removable end cap - removed as used in this invention |
| 16. | Trans-resistance amplifier for first radiation detector |
| 16A. | Feedback resistor $R_{16}$ (determines trans-resistance gain) |
| 17. | Trans-resistance amplifier for second radiation detector |
| 17A. | Feedback resistor $R_{17}$ (determines trans-resistance gain) |
| 18. | Dual-channel data-acquisition system |
| 18A. | Summing circuit or computer algorithm producing the sum (or average) of signals from first plus second radiation detector |
| 18B. | 'Difference' circuit or computer algorithm producing the difference of first detector signal minus second detector signal or, preferably, the normalized difference, i.e., the difference divided by the sum. |
| 19. | Visual display (analog meter, alpha-numeric display panel, computer screen, etc.) |
| 20. | Sliding carriage or vernier stage |

DETAILED DESCRIPTION OF THE PREFERRED EMBODIMENTS

Figure 2:
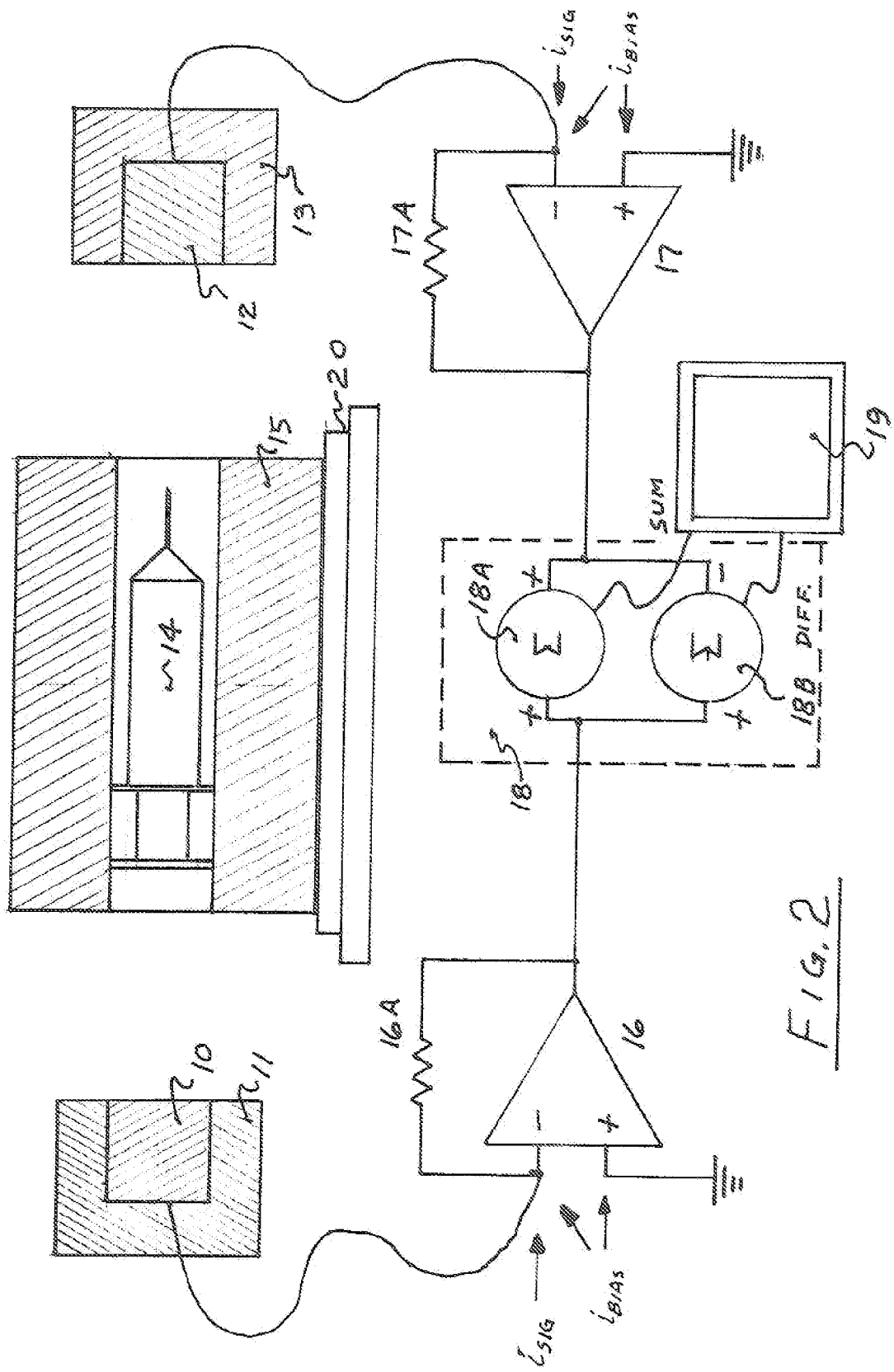
FIG. 2 is a schematic representation of a radiation dose calibrator in accordance with the present invention.

A new implementation of a radiation dose calibrator 21 in accordance with the present invention is shown schematically in FIG. 2. A first radiation detector 10 and a second radiation detector 12 are placed a predetermined distance apart and aligned on a common axis A-A'. Each detector produces an electrical current which is proportional to the time-rate of energy absorbed by the detectors, emanating from a vial or syringe 14 filled with radioactivity. A vial/syringe shield 15—usually constructed of a dense element such as lead or tungsten—is a three-part design, commonly used for transport of radio-pharmaceuticals used in nuclear medicine, in which both end caps 15a and 15b of the shield 15 may be detached from the central body in order to access the syringe needle and the plunger 14.

This shield can be quite heavy, so it may be conveniently placed on a manually-adjusted or motor-driven sliding carriage or vernier stage 20 in order to facilitate accurate placement. During the measurement procedure, the radioactive sample 14 is preferably aligned on axis A-A' between detectors 10 and 12.

Rather than using air-filled or gas-filled chambers, the detectors 10, 12 preferably employ solid materials such as scintillating crystals or plastics. In a scintillation detector, energetic gamma ray photons interact within a special crystal or plastic material to produce flashes of light (scintillations). The scintillating crystal or plastic is coupled to a photo-electric transducer such as a photo-multiplier tube or—in a preferred embodiment—a Silicon photo-diode that converts light energy to electric current which, in turn, may be amplified and converted to a more conveniently measured voltage signal. Detectors can also be constructed wherein energetic gamma ray photons interact directly (without requiring a scintillator) in a solid-state semiconductor material such as Silicon, Cadmium Telluride, etc. to produce an electric current.

Following common practice, the radiation-induced current generated by each detector, $I_{sig}$, is applied to the input of a corresponding trans-resistance amplifier 16, 17 employing a high-gain operational amplifier (or functional equivalent). Each trans-resistance amplifier has a corresponding feedback resistor 16A, 17A whose value is designated $R_{16}$ and $R_{17}$, respectively. In normal practice, $R_{16}$ and $R_{17}$ would have the same nominal value. Each amplifier produces a voltage across its respective feedback resistor (or, equivalently, a current through its feedback resistor) such that the potential at the inverting input terminal is forced to equal 'zero' to match the potential at the non-inverting (+) terminal (shown grounded, i.e., at 'zero' potential). The gain of trans-resistance amplifier 16 is numerically equal to the value of $R_{16}$, expressed in ohms. The voltage at the output of trans-resistance amplifier 16 is given by $V_{16}(out) = -I_{sig} \times R_{16}$. A corresponding relation holds for the voltage at the output of trans-resistance amplifier 17.

All amplifiers require a small but finite bias current flowing in (or out) of both (+) and (−) input terminals in order to operate correctly. In the trans-resistance amplifiers shown in FIG. 2, the bias current, $i_{bias}$, can introduce an error term which fluctuates with changes in ambient temperature. The smallest amount of radioactivity that can be measured reliably is governed by such temperature-induced base-line fluctuations. As a practical matter, $i_{bias}$ should be substantially less than the radiation-induced detector current $i_{sig}$. Operational amplifiers with the smallest bias currents are therefore preferred for this application—for example, the LMC6000 series of operational amplifiers from National Semiconductor Corp. specify $i_{bias}$ of a few 10's of femto-amperes at room temperature.

Voltage signals from the respective amplifier outputs are applied to separate inputs of a 2-channel electronic data acquisition apparatus 18. An analog summing circuit or numerical computing apparatus 18A generates the sum of the two voltages (or equivalently, the average of the two voltages). This signal sum (or average) is proportional to the amount of radio-activity contained in the syringe. Moreover, as explained below, the difference between the two voltages (or equivalently, the difference divided by the sum) derived from difference circuit 18B can indicate a relative degree of accuracy of placement of the radioactive sample between the two detectors, such that the two detector signals are equal. A reading of 'zero' difference denotes perfect signal balance.

Detector Properties: The advantage of a detector made of solid material, compared with an ionization chamber of the prior art, is that the mass—and hence the capacity to absorb radiation (stopping power)—of a solid detector is much greater than an equivalent volume of air in an ion chamber so that, for a given radiation intensity and a given detector volume, the solid detectors can provide a substantially larger signal current. In the arrangement shown in FIG.2, the detectors are implemented as 'DC current mode' detectors used for measuring doses of radioactivity typically employed in medicine. The arrangement is relatively simple in its implementation and, since it does not actually 'count' individual absorbed photons, it does not suffer from 'pulse pile-up' or 'system dead-time' count-rate distortion effects.

It does, however, require care in its design and construction to produce the required precision and stability of readings, since, depending on the size and spacing of the detectors, the detector currents are still rather small. For example, to establish a credible lower-limit of detection sensitivity, we placed a 10 micro-curie (370,000 becqerel) check-source ($^{137}$Cs isotope with principal emission line=662 KeV) at a distance of 30.5 cm from a 22 mm diameter×22 mm long Thallium Activated Cesium Iodide scintillation crystal which, in turn, is optically-coupled to a 1 square cm Si PIN photodiode (Hamamatsu S3590-08). We then recorded a photo-current from the Si PIN diode of ~200 femto-amperes. The feedback resistor (and hence the gain-factor) R, was one gig-ohm (one billion ohms) and thus produced a voltage signal at the output of the amplifier of ~0.2 millivolt.

A normal dose of radioactive material intended for patient diagnostic purposes would contain on the order of 1000 times more activity, producing a correspondingly greater signal. However, it is understood that for certain specialized applications a substantially more complex 'counting-type' of detector may be preferred for measuring minute amounts of radioactivity (very low doses), and in situations where it may be necessary to select one particular radioactive species and to discriminate against interfering or unwanted species using additional apparatus and more sophisticated techniques. In the case of a counting type detector, care must be taken to minimize (or compensate for) errors and distortions in readings due to 'pulse pile-up' and system 'dead time' losses. The particular choice of detector configuration and material composition is governed by the particular end-use, and by technical and cost-benefit design trade offs which are well-understood by those schooled in the art.

To summarize: When compared with an air-filled or gas-filled ion chamber, the high detection efficiency of a solid detector provides substantially faster, and potentially more accurate, measurements, while at the same time allowing for a substantially more compact—and hence much easier to shield—physical implementation. In fact, the detectors themselves only require shielding which is sufficient to prevent false readings due to ambient or scattered radiation from nearby objects and from the laboratory surroundings. 'Heavy' shielding for personnel protection may thus be concentrated primarily around the radioactive vial or syringe being measured.

Homogeneity of response along the axis: Assume for the time being that the radioactive source is approximated by a 'point', i.e., the cross-sectional area of the source is 'small' relative to the cross-sectional area of the detectors. It is well-known by those schooled in the art that each detector's response to a point source of radioactivity varies inversely as the square of the distance between source and detector. Thus, each individual detector's output current depends not only on the amount of radioactivity, but also the distance from the source to the detector. Therefore, it is an object of this invention to define a configuration in which the variation in detector signal current is constrained within predetermined—and acceptable—tolerance limits, while also allowing for inevitable small displacements of the source within a prescribed volumetric 'envelope'.

Assuming identical detector characteristics and uniform geometry, the sweet spot—or region where the detector's response is nearly invariant with respect to small changes in source position along the axis—is located at the center of symmetry, where the two detector signals are exactly equal in amplitude.

A simple analytic model: For the sake of simplicity, assume there is no attenuating or scattering medium between source and detector(s). In the preferred embodiment, the two detectors are made to be identical in their physical and operational characteristics, so that when the radioactive source is placed at the physical center of symmetry, the electrical currents from the two detectors are essentially equal.

If the detectors are not identical, or if the shield geometry is not uniform and symmetrical, there will still be a 'sweet spot'—though not necessarily at the physical center of symmetry.

Figure 3:
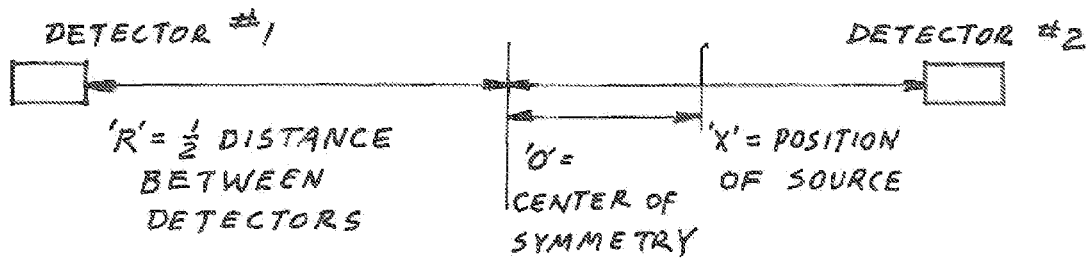
FIG. 3 graphically illustrates the level of detector response as a function of displacement of a point source of radioactivity from the center of symmetry.
Figure 3:
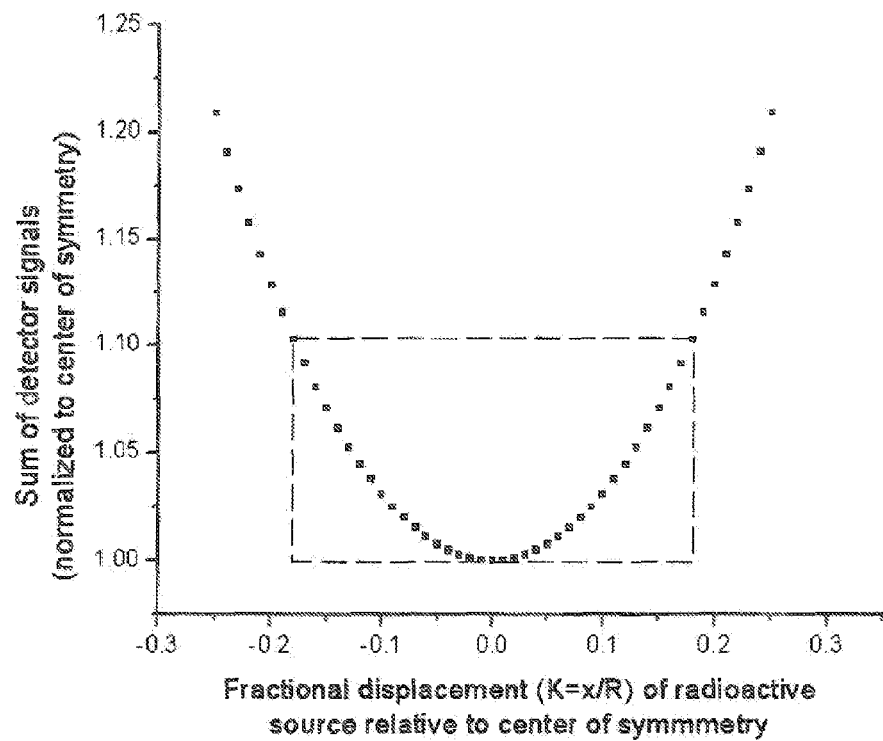

Let R=the half-distance between the two detectors;
Express the source displacement X (relative to the center of symmetry) as a fraction of R, i.e.,
X=kR, where the parameter k varies from −1 to +1.
Let Y=sum of the signals from Detector #1+Detector #2.
Let $Y_0$=the value of Y when the radiation source is placed at X=0, the center of symmetry.
$(Y-Y_0)$ is the deviation of Y from its value at X=0
The fractional deviation, relative to the deviation at X=0, is
$(Y-Y_0)/Y_0=(\frac{1}{2})[1/(1+k)^2+1/(1-k)^2]-1$
The deviation relative to the value (normalized to unity) at the center of symmetry, and plotted in FIG. 3 is:

$$1+(Y-Y_0)/Y_0=(\tfrac{1}{2})[1/(1+k)^2+1/(1-k)^2]$$

Numerical Example: Suppose R—the source-to-detector distance—is 30 cm (~1 ft.), then a plus 10%/minus 0% tolerance 'window' in the plot in FIG. 3 corresponds to plus and minus 0.18×30 cm=5.4 cm or ~2 inches, about the center of symmetry, or approximately 4 inches in overall length.

Verification of symmetry: The dual-detector configuration provides a convenient and rapid means of verifying symmetry of placement of the source being measured. In the example cited above, the center of the 'sweet spot' occurs exactly at the physical center of symmetry (assuming both detector channels have identical gain and geometric response). When the difference between the signals from detector #1 and detector #2 is 'zero', then the source is properly centered in the direction along the axis A-A'. This difference signal can also be used in a feed-back control system to actuate a motor-driven sliding carriage to automatically seek and maintain centering of the radioactive sample.

Detector Standardization: In the event the detectors are not identical due, for example, to slight differences in formulation of the scintillation crystals, slight differences in the optical coupling efficiency between crystal and photo-diode, photo-multiplier tube, or other photo-electric transducer, slight differences in transducer efficiency, amplifier circuit gain, etc., some means of adjustment of detector 'balance' is desired. A further provision for adjustment of the overall detector system gain is required to calibrate the apparatus using a known standard 'dose' of the isotope being measured, contained in an appropriate, standardized vial or syringe.

Collimating Shields: In some cases it may be useful to embed the detectors more deeply inside their shields so as to effect collimating shields which may further help to reduce the response to ambient radiation, or the effects of 'scatter' from nearby objects. The deeper the collimator, the more 'peaked' is the detectors' response to variations in source placement in the transverse plane; i.e., moving the radioactive source away from the detector's central axis will cause a reduction in the detector signal(s).

In designing a practical system, one would perform a similar calculation (or model experiment, or computer simulation) as above to derive the variation in detector signal versus fractional displacement in directions transverse to the axis of symmetry. One would then construct a surface map of detector response versus deviation from the center of symmetry, thus defining a 'volumetric envelope' or 'box' of pre-determined tolerance such as shown above, which demonstrates that as long as the radioactivity source is constrained within the location and dimensions of the 'envelope' or 'box', then the detector response (within the pre-determined tolerance) to a point source of radioactivity depends only on the amount of activity contained in the source.

Extended Sources: Finally, the model example above implies that the detector's response to an extended source such as a fluid-filled vial or syringe will also be proportional to the amount of radioactivity and will not depend on the particular physical shape, or volume of the fluid-filled vial or syringe (within the predetermined tolerance), provided the vial or syringe fits within the prescribed spatial 'envelope' of the detector system response.

In actual practice, the variation in the dual-detectors' response to small physical displacements of a vial or syringe relative to the center of the 'sweet spot' is actually less (i.e., more 'flat') than predicted by the example above, due to an averaging effect over the volume of the vial or syringe. Thus, the above example represents a somewhat pessimistic, or conservative, limit of measurement tolerance, provided all system calibrations and measurements are done using standardized vials or syringes filled to the same (nominal) fluid volume.

Summary, Ramifications, and Scope of the Invention: A new radioactivity dose calibrator system for measuring the quantity of radioactive material contained in a sample-vial or syringe, without removing the vial or syringe from its primary radiation shield, simplifies material handling and greatly reduce personnel exposure to radiation in a busy nuclear pharmacy.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A radioactivity dose calibrator comprising:
   a transportable radiation shield-container comprising radiation-absorbing material, having a reference axis centered on a corresponding bore cavity for receiving a vial or syringe containing radioactive material, the walls of said shield-container absorbing radiation emitted by said radioactive material, said shield-container having first and second removable end portions, thereby allowing radiation emitted by said radioactive material to be directed substantially along said reference axis in two directions;
   first and second radiation detectors disposed on said reference axis, and located a pre-determined distance apart and facing adjacent respective first and second open ends of said radiation shield-container, wherein said first and second detectors are responsive to radiation emitted by the radioactive material, and provide first and second output signals respectively representing the amount of radiation received by said first and second detectors from the radioactive material;
   a signal processing circuit coupled to said first and second detectors for comparing the sum of said first and second output signals with a reference signal level and providing a third output signal representing a calibrated level of radioactivity emitted by the radioactive material; and
   display means coupled to said signal processing circuit and responsive to said third output signal for providing a visual indication of the calibrated level of radioactivity emitted by the radioactive material.

2. The radioactivity dose calibrator of claim 1, wherein said first and second radiation detectors are scintillation detectors, each incorporating a scintillating crystal, scintillating plastic, or liquid scintillator, and optically coupled to an electro-optical transducer such as a photo-diode or photo-multiplier tube.

3. The radioactivity dose calibrator of claim 1, wherein said first and second radiation detectors are semiconductor devices which directly convert incident radiation energy into electrical current.

4. The radioactivity dose calibrator of claim 1, further incorporating a transport arrangement for moving the radioactive material along said reference axis toward or away from said first and second detectors.

5. The radioactivity dose calibrator of claim 4, wherein said transport arrangement includes a sliding carriage supporting said radiation shield-container.

6. The radioactivity dose calibrator of claim 5, wherein said sliding carriage is manually moved or motor driven.

7. The radioactivity dose calibrator of claim 6, wherein said sliding carriage further includes a manual or motor-driven vernier adjustment mechanism for precisely setting the position of the radioactive material along the reference axis.

8. The radioactivity dose calibrator of claim 7, wherein said motor-driven vernier adjustment mechanism is actuated by a control signal derived from the difference between said first and second radiation detector output signals.

9. A radioactivity dose calibrator comprising:
   a transportable radiation shield-container comprised of radiation-absorbing material, having a reference axis centered on a corresponding bore cavity for receiving a vial or syringe containing radioactive material, the walls of said shield-container absorbing radiation emitted by said radioactive material, said shield container having first and second removable end portions, thereby allowing radiation emitted by said radioactive material to be directed substantially along said reference axis in two directions;
   first and second radiation detectors disposed on said reference axis, and located a pre-determined distance apart and facing adjacent respective first and second open ends of said radiation shield-container, wherein said first and second detectors are responsive to radiation emitted by the radioactive material, and provide first and second output signals respectively representing the amount of radiation received by said first and second detectors; and
   a signal summing circuit coupled to said first and second detectors for providing a signal representing the sum of said first and second output signals, wherein said signal representing said sum is relatively invariant with respect to small displacements of the radioactive material along said reference axis relative to a position on said axis at which said first and second detector signals are equal in amplitude.

10. The radioactivity dose calibrator of claim 9, further comprising a display means coupled to said signal processing circuit and responsive to said sum and difference signals for providing, respectively, a first visual indication of the radioactivity level of the radioactive material and a second visual indication of the location of the radioactive material on said reference axis between the first and second detectors relative to the location where said first and second detector output signals are equal.

11. A radioactivity dose calibrator comprising:
a transportable radiation shield-container comprised of radiation-absorbing material, and having a reference axis centered on a corresponding bore-cavity for receiving a vial or syringe containing radioactive material, the walls of said shield-container absorbing radiation emitted by said radioactive material, said shield-container having first and second removable end portions, thereby allowing radiation emitted by said radioactive material to be directed substantially along said reference axis in two directions;
first and second radiation detectors disposed on said reference axis, and located a pre-determined distance apart and facing adjacent respective first and second open ends of said radiation shield-container, wherein said first and second detectors are responsive to radiation emitted by the radioactive material for providing first and second output signals respectively representing the amount of radiation received by said first and second detectors from the radioactive material;
a signal processing circuit coupled to said first and second detectors and responsive to said first and second output signals for generating a sum signal comprising the addition of said first and second output signals, wherein said sum signal is proportional to the radioactivity level of the radioactive material, said signal processing circuit also generating a difference signal derived from the difference between said first and second output signals, wherein said difference signal indicates the position of the radioactive material relative to a location on said reference axis between first and second detectors at which said first and second radiation detector output signals are equal.

12. The radioactivity dose calibrator of claim 11, wherein the polarity and amplitude of said difference signal indicates the position of the radioactive relative to a location on said reference axis between said first and second detectors at which said first and second radiation detector output signals are equal.

* * * * *